(12) United States Patent
Chen et al.

(10) Patent No.: US 7,579,482 B2
(45) Date of Patent: Aug. 25, 2009

(54) STRUCTURE OF CAMPHOR-DERIVED CHIRAL AUXILIARY AND METHOD FOR FORMING THE SAME

(75) Inventors: Kwunmin Chen, Taipei (TW); Jung-Hsuan Chen, Taoyuan (TW)

(73) Assignee: National Taiwan Normal Univeristy, Taipei (TW)

( * ) Notice: Subject to any disclaimer, the term of this patent is extended or adjusted under 35 U.S.C. 154(b) by 356 days.

(21) Appl. No.: 11/122,036

(22) Filed: May 5, 2005

(65) Prior Publication Data

US 2006/0252941 A1    Nov. 9, 2006

(51) Int. Cl.
*A61K 31/416* (2006.01)
*C07D 487/18* (2006.01)

(52) U.S. Cl. .................... 548/359.1; 514/387
(58) Field of Classification Search ............. 548/359.1, 548/302; 514/405, 387
See application file for complete search history.

(56) References Cited

OTHER PUBLICATIONS

Yang, et al, Tetrahedron Letters, 41 (2000) 1453-1456.*
Chapuis, et al., Tetrahedron: Asymmetry, 11 (2000)4581-4591.*
Yang et al., Organic Letters, 2(6) (2000) 729-731.*
Yang, et al., J. Org. Chem., 66 (2001) 1676-1679.*
Pan, et al., Tetrahedron Letters 45 (2004) 2541-2543.*

Accession No. 1963:20867, CAPLUS abstract of Kuusinen, T et al. "Cyclofenchenecarboxylic acid," Suomen Kemistilehti B (1962), 35B (No. 3).*
Accession No. 1963:20866 CAPLUS abstract of Witek, S. et al, "Sulfate Turpentine. I. Composition of the 155-86 degree terpenes fraction." Chem. Stosowana (1962), vol. 6.*

* cited by examiner

*Primary Examiner*—Joseph K. McKane
*Assistant Examiner*—Janet L Coppins
(74) *Attorney, Agent, or Firm*—WPAT, PC; Justin I. King

(57) ABSTRACT

The present invention discloses a structure of camphor-derived chiral auxiliary with a general formula (I),

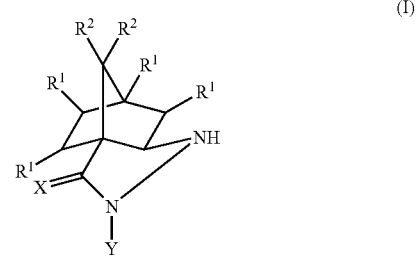

wherein $R^1$ and $R^2$ groups are independently hydrogen or $C_1$ to $C_{10}$ alkyl, X group is oxygen, two hydrogen atoms, or sulfur, and Y group is a functional group with stereo effect. Moreover, this invention also discloses a method for forming the above-mentioned chiral auxiliary.

22 Claims, No Drawings

STRUCTURE OF CAMPHOR-DERIVED CHIRAL AUXILIARY AND METHOD FOR FORMING THE SAME

BACKGROUND OF THE INVENTION

1. Field of the Invention

The present invention is generally related to structures of asymmetric compounds, and more particularly to structures of camphor-derived chiral auxiliary and the method for forming the same.

2. Description of the Prior Art

A survey by Frost & Sullivan estimates that global sales of single-enantiomer compounds are expected to reach $8.57 billion by the end of 2004, $9.5 billion by 2005, and $14.94 billion by 2009, growing annually by 11.4%. Furthermore, chiral industry could be divided into two groups: manufacturing of chiral compounds and analysis of chiral compounds, wherein manufacturing of chiral compounds dominate most of the market, and manufacturing of chiral compounds could be further divided into chiral synthesis and chiral separation. Comparing to chiral separation, the marker size of chiral synthesis is much bigger. Additionally, according to the selling report (from "CHIRAL CHEMISTRY", Chemical & Engineering Story, Jun. 14, 2004, Volume 82, Number 24, pp. 47-62), in nine of top 10 drugs, the active ingredients are chiral. Therefore, chiral compound plays an important role in pharmacy.

A variety of reactions can be catalyzed by specially-designed chiral auxiliaries, wherein many products, such as drug intermediates, are fabricated with high diastereoselectivity. A well known example is that American company Monsanto employed a forming method, developed by Knowles, W. S., to produce a drug treatment for Parkinson's Disease (PD), and this drug is L-DOPA [(3,4-dihydroxyphenyl)-L-alanine]. Patients with PD are lack of dopamine (DA) in basal ganglia in their brain. Moreover, in the animal and human body L-DOPA was enzymatically converted to DA, and that's why L-DOPA is chosen to be the treatment for PD. In the research field based on Knowles, after more than thirty years' development, chemists have successfully prepared hundreds and hundreds chiral auxiliaries and catalysts, which are applied in many organic reactions. Therefore, optically active products from those organic reactions are obtained in relative high enantiomeric purity.

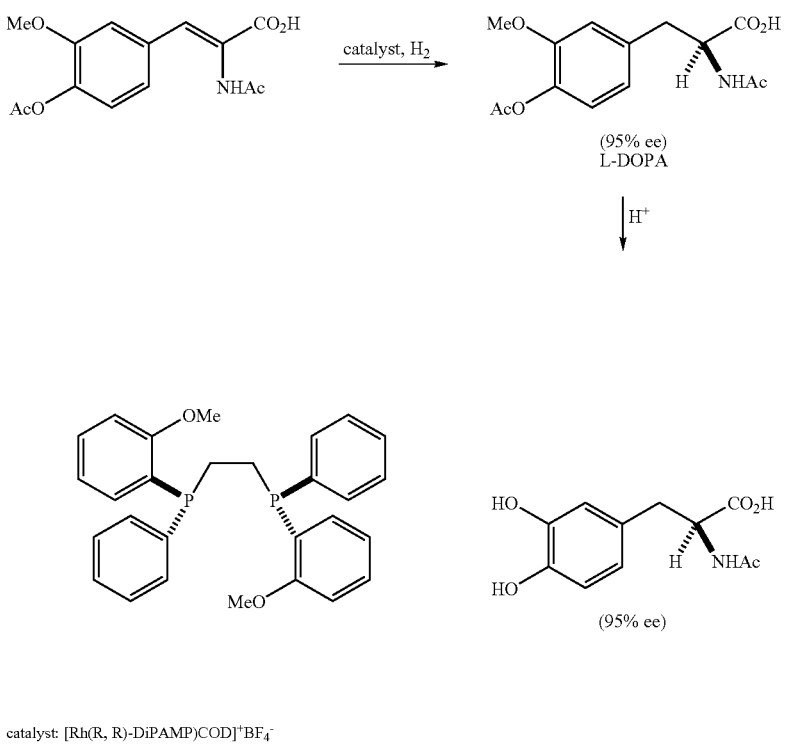

It is another example demonstrated that Oppolzer's camphor sultam serves as an effective chiral auxiliary for optically active products. The group of Bernard P. ROQUES in 1995 has already reported that 4-phosphonomethyl-phenylalanine (Pmp) was successfully prepared by using derivatives of Oppolzer's camphor sultam. Phosphorylation and dephosphorylation reactions on tyrosine residues of proteins play important roles in cellular signal transduction. These processes are mediated by proteins endowed with tyrosine kinase (PTK) and phosphatase (PTP) enzymatic activities. The aberrant expression of PTK and PTP can lead to neoplastic cell transformation. It is therefore of great interest to develop inhibitors of these recognition process in order to study the signaling pathways and to search for potential antitumor agents. This could be done by using small peptides derived from the enzyme sequence surrounding the O-phosphotyrosine residue, and the stable analoge 4-phosphonomethyl-phenylalanine (Pmp) was proposed as an hydrolytically stable analogue of O-phosphotyrosine. As shown in the following scheme, good stereocontrol of Pmp has been achieved by using derivatives of Oppolzer's camphor sultam as chiral auxiliary.

derivative with the initiator to introduce a functional group with stereo effect into the wanted compound. Then, a cyclization reaction (amidation) is performed to fabricate a first chiral auxiliary. Moreover, another object of the present invention is to employ an elimination reaction of the above-mentioned first chiral auxiliary with a Lewis base without hydroxyl group to produce a second chiral auxiliary. The fabrication method disclosed in this invention did have the advantages of simple procedure, good selectivity, and high yield. Therefore, this present invention does have the economic advantages for industrial applications.

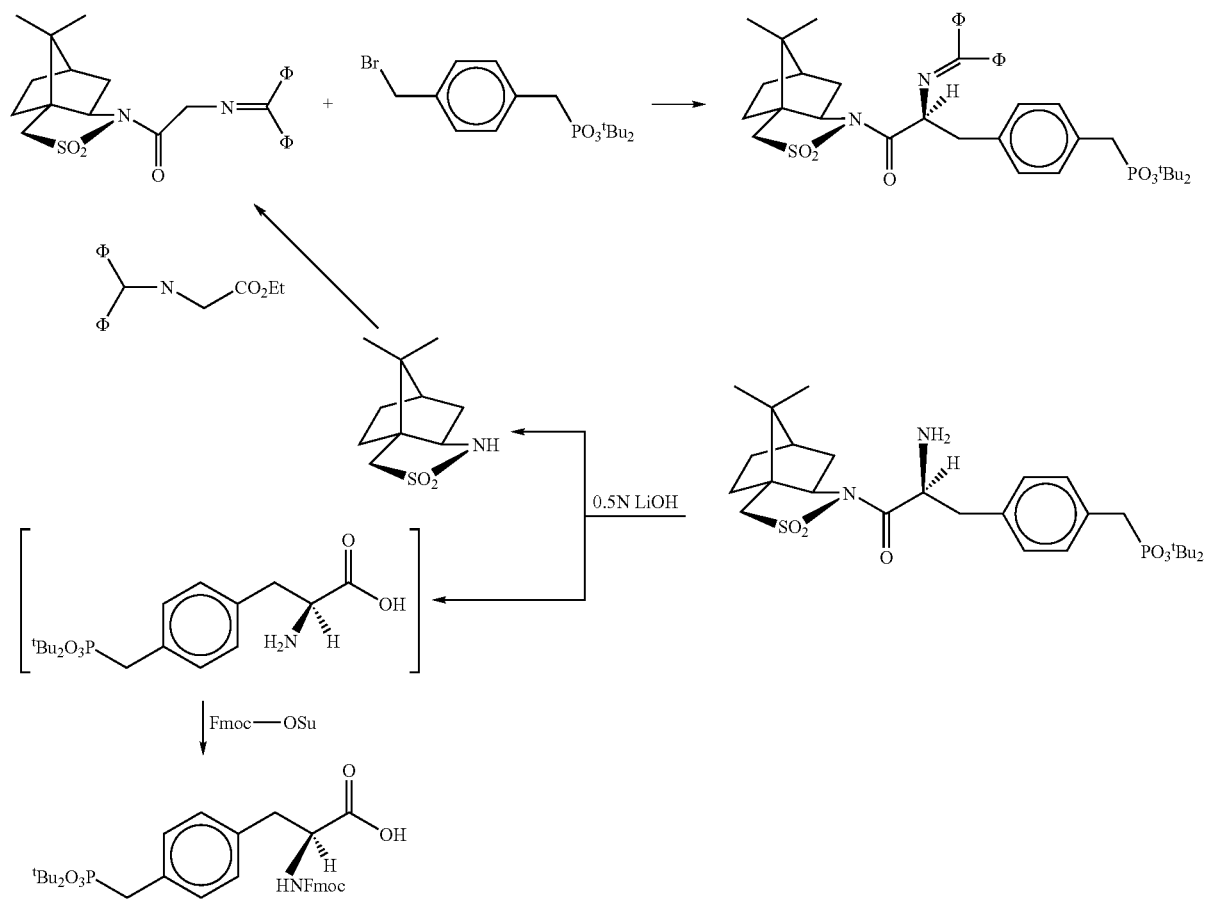

In summary, chiral auxiliaries hold considerable potential for the asymmetric synthesis. At present, most commercial chiral auxiliaries face some problems that decelerate the growth rate of the market, such as high cost and complicated forming method. On the other hand, if recovery amount of used chiral auxiliary can be raised significantly, the operational cost will be reduced efficiently. In addition, as environmental issues have become highly regarded nowadays, new and appreciate structures of camphor-derived chiral auxiliary and the method for forming the same, is no doubt the trend in the future.

SUMMARY OF THE INVENTION

In accordance with the present invention, a new structure of camphor-derived chiral auxiliary and the method for forming the same is provided to correspond to industrial utilizations.

One object of the present invention is to employ an initiator which is commercially available, and by reacting a hydrazine Accordingly, the present invention discloses a structure of camphor-derived chiral auxiliary with a general formula (I),

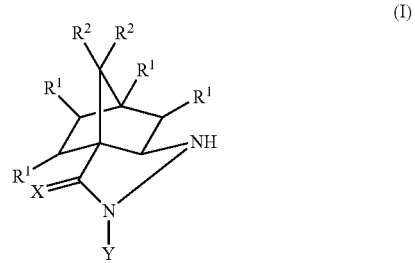

(I)

wherein $R^1$ and $R^2$ groups are independently hydrogen or $C_1$ to $C_{10}$ alkyl, X group is oxygen, two hydrogen atoms, or sulfur, and Y group is a functional group with stereo effect. Moreover, this invention also discloses a method for forming the above-mentioned chiral auxiliary.

DESCRIPTION OF THE PREFERRED EMBODIMENTS

What is probed into the invention is structures of camphor-derived chiral auxiliary and the method for forming the same. Detailed descriptions of the production, structure and elements will be provided in the following in order to make the invention thoroughly understood. Obviously, the application of the invention is not confined to specific details familiar to those who are skilled in the chiral auxiliary. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first preferred embodiment of this invention, there is provided a chiral auxiliary with a general formula (I),

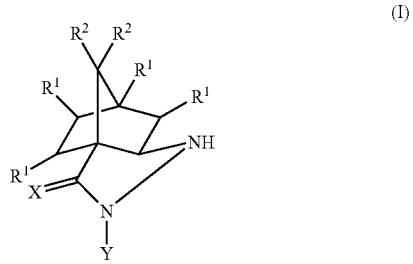

(I)

wherein $R^1$ and $R^2$ groups are independently hydrogen or $C_1$ to $C_{10}$ alkyl, X group is oxygen, two hydrogen atoms, or sulfur, and Y group is a functional group with stereo effect. More preferred are those moieties where the $R^1$ groups are hydrogen, the $R^2$ groups are methyl, and the X group is oxygen. Additionally, the Y group is with the following structure,

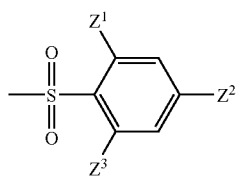

$Z^1$, $Z^2$ and $Z^3$ are independently selected from the group consisting of: H, $CH_3$, $CH(CH_3)_2$, I, Br, Cl, nitrile group, OR, NR, $NO_2$, phenyl group, allyl group, wherein R is alkyl group. More preferred is this moiety where the Y group is p-toluenesulfonyl (Ts; thereinafter called Ts) with the following structure:

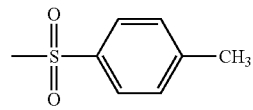

In a second preferred embodiment of this invention, a method for forming a chiral auxiliary is provided. First of all, an initiator with the following structure is provided:

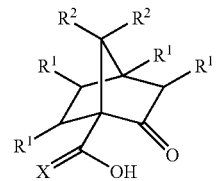

Wherein $R^1$ and $R^2$ groups are independently hydrogen or $C_1$ to $C_{10}$ alkyl, X group is oxygen, two hydrogen atoms, or sulfur. More preferred are those moieties where the $R^1$ groups are hydrogen, the $R^2$ groups are methyl, and the X group is oxygen. Next, a hydrazine derivative $H_2NNHY$ is provided, wherein Y group is a functional group with stereo effect, as described in the first preferred embodiment. Then, a dehydration reaction is performed of the hydrazine derivative $H_2NNHY$ with the initiator to produce an imine with the following structure,

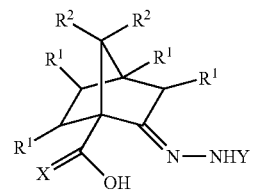

When the initiator is used in an amount of 1 equivalent, the hydrazine derivative $H_2NNHY$ is used in an amount more than 1 equivalent, and a preferred amount of $H_2NNHY$ is 1.2 equivalents. On the other hand, the dehydration reaction is performed in dichloromethane ($CH_2Cl_2$), and the operation temperature of the dehydration reaction ranges from 25° C. to 30° C.

In this embodiment, after the dehydration reaction, a cyclization reaction of the imine is performed to produce a amide with the following structure,

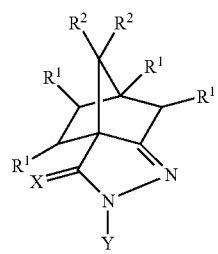

The cyclization reaction is a one-pot reaction. In a better case of this embodiment, the cyclization reaction further comprises an acylhalogenation step and a dehalogenation step, wherein the acylhalogenation step is performed to react $SOZ_2$, wherein Z is F, Cl, Br or I, with the imine to produce a mediate with the following structure:

When the imine is used in an amount of 1 equivalent, the $SOZ_2$ is used in an amount more than 2 equivalents, and a preferred amount of the $SOZ_2$ is 2.4 equivalents. Moreover, in this better case, the cyclization reaction is performed in ethyl acetate (EA), and the operation temperature of the cyclization reaction ranges from 50° C. to 80° C.

In this embodiment, after the cyclization reaction, a reduction reaction is performed of the amide with a reducing agent to produce the chiral auxiliary with the following structure, (I)

In another better case of this embodiment, the reducing agent further comprises sodium cyanoborohydride ($NaCNBH_3$). When the amide is used in an amount of 1 equivalent, the reducing agent is used in an amount more than 15 equivalents, and a preferred amount of the reducing agent is 18 equivalents. Moreover, the reduction reaction is performed in acetic acid (AcOH), and the operation temperature of the reduction reaction ranges from 25° C. to 30° C.

EXAMPLE 1

As shown in scheme 1, (+)-ketopinic acid 1 (20.00 g, 109.76 mmole) was dissolved in 150 mL $CH_2Cl_2$. Next, p-toluenesulfonhydrazide ($H_2NNH$-Ts) (28.62 g, 153.66 mmole) was added, under a nitrogen atmosphere, and the temperature is kept on room temperature (from 25° C. to 30° C.). After stirring for approximately 1 hr, the resulting solution is clear. The reaction was then quenched via addition of water. The organic layers were extracted with $CH_2Cl_2$, dehydrated with anhydrous magnesium sulfate. After filtration and primary drying, products are washed by cyclohexane and $CH_2Cl_2$ for 2 or 3 times, and then vacuum dried to form white solid 2. Finally, white solid 2 was recrystallied to form a colorless and transparent solid (36.54 g, yield 95%).

$^1$H NMR:

$^1$H NMR ($CDCl_3$, 200 MHz) δ 7.83 (d, J=8.4 Hz, 2H), 7.34 (d, J=8.2 Hz, 2H), 2.57-2.31 (m, 2H), 2.42 (s, 3H), 2.04-1.95 (m, 3H), 1.66 (td, J=9.8, 3.6 Hz, 1H), 1.35-1.20 (m, 1H), 1.16 (s, 3H), 0.79 (s, 3H)

$^{13}$C NMR:

$^{13}$C NMR ($CDCl_3$, 200 MHz) δ 171.9, 169.0, 145.0, 134.3, 130.1, 128.3, 127.9, 61.1, 51.7, 44.3, 33.9, 31.1, 27.5, 21.5, 19.7

HRMS:

Found: 350.1283 (calcd for $C_{17}H_{22}N_2O_4S$ 350.1300)

Compound 2 (9.00 g, 25.70 mmole) was dissolved in 660 mL ethyl acetate (EA). Next, $SOCl_2$ (7.34 g, 61.69 mmole) was added, heated to 60° C. to 80° C., and reflux for 5 hrs. The reaction was then quenched via addition of water. The organic layers were extracted with EA, dehydrated with anhydrous magnesium sulfate. After filtration and vacuum drying, products are purified by column chromatography with eluant (hexane:ethyl acetate=3:1) to form compound 3 (6.66 g, yield 78%). Finally, compound 3 was recrystallied to form a colorless and transparent solid.

$^1$H NMR:

$^1$H NMR ($CDCl_3$, 200 MHz) δ 7.87 (d, J=7.4 Hz, 2H), 7.29 (d, J=8.4 Hz, 2H), 2.60-2.51 (m, 1H), 2.39 (s, 3H), 2.25-2.00 (m, 4H), 1.67 (td, J=9.8, 3.4 Hz, 1H), 1.45 (td, J=9.2, 3.8 Hz, 1H), 1.07 (s, 3H), 0.57 (s, 3H)

$^{13}$C NMR:

$^{13}$C NMR ($CDCl_3$, 200 MHz) δ 176.2, 172.8, 145.2, 135.3, 129.7, 127.9, 64.0, 50.9, 48.7, 32.2, 26.8, 26.0, 21.5, 18.5, 18.1

X-ray Crystallographic Analysis:

Crystal data for 3.$H_2O$ at 25° C.: $C_{17}H_{20}N_2O_3S$, M332.422, Orthorhombic, $P2_12_12_1$, a=10.1101 (2)Å, b=12.9076 (3)Å, c=25.9674 (8)Å, V=3388.67 (15)Å$^3$, Z=8, λ=0.71073 Å, $D_x$=1.303 Mg/m$^3$, μ=0.21 mm$^{-1}$, 2336 reflections, 416 parameters, R=0.093, $R_w$=0.096 for all data.

HRMS:

Found: 332.1190 (calcd for $C_{17}H_{20}N_2O_3S$ 332.1195)

Compound 3 (4.00 g, 12.04 mmole) was dissolved in 60 mL acetic acid (AcOH). Next, $NaCNBH_3$ powders (13.62 g, 216.79 mmole) were added for several batches. In the first batch, part of $NaCNBH_3$ powders was added, under a nitrogen atmosphere, and the temperature is kept on room temperature (from 25° C. to 30° C.), then followed by TLC. After all of the $NaCNBH_3$ powders were added, The reaction was then quenched via addition of water. The organic layers were extracted with $CH_2Cl_2$, dehydrated with anhydrous magnesium sulfate. After filtration and vacuum drying, products are purified by column chromatography with eluant (hexane: ethyl acetate=2:1) to form compound 4 (3.86 g, yield 96%). Finally, compound 4 was recrystallied to form a colorless and transparent solid.

$^1$H NMR Analysis:

$^1$H NMR ($CDCl_3$, 200 MHz) δ 7.94 (d, J=8.4 Hz, 2H), 7.33 (d, J=8.4 Hz, 2H), 3.49 (dd, J=8, 4.4 Hz, 1H), 2.44 (s, 3H), 2.15-1.99 (m, 2H), 1.90-1.80 (m, 2H), 1.67 (dd, J=13.2, 8.4 Hz, 1H), 1.29-1.16 (m, 2H), 0.94 (s, 3H), 0.77 (s, 3H)

$^{13}$C NMR Analysis:

$^{13}$C NMR ($CDCl_3$, 200 MHz) δ 172.4, 145.3, 134.7, 129.5, 128.6, 64.7, 59.0, 52.5, 47.2, 36.4, 29.0, 26.5, 21.6, 20.5, 19.7

X-ray Crystallographic Analysis:

Crystal data for pps-1.$H_2O$ at 25° C.: $C_{17}H_{22}N_2O_3S$, $C_{17}H_{22}N_2O_3S$, M 334.438, Monoclinic, $P2_1$, a=9.7297 (3)Å, b=14.6999 (4)Å, c=12.2705 (5)Å, V=1714.77 (10)Å$^3$, Z=4, $D_x$=1.295 Mg/m$^3$, μ=0.205 mm$^{-1}$, 5864 reflections, 415 parameters, R=0.0999, $R_w$=0.1829 for all data.

HRMS:

Found: 334.1350 (calcd for $C_{17}H_{22}N_2O_3S$ 334.1351)

SCHEME 1

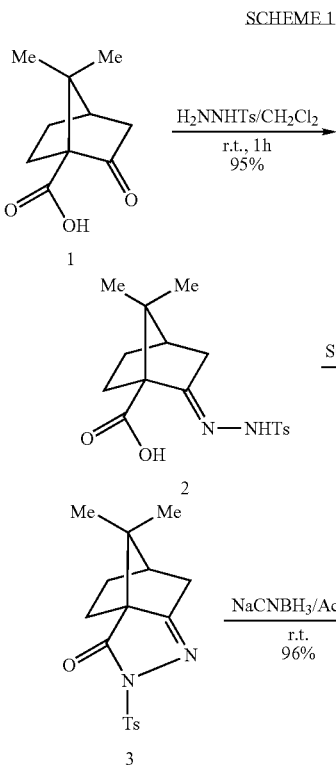

In a third embodiment of this invention, there is provided a chiral auxiliary with a general formula (II),

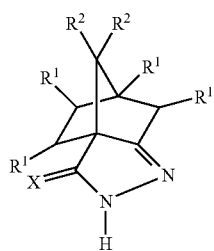

(II)

wherein $R^1$ and $R^2$ groups are independently hydrogen or $C_1$ to $C_{10}$ alkyl, and X group is oxygen, two hydrogen atoms, or sulfur. More preferred are those moieties where the $R^1$ groups are hydrogen, the $R^2$ groups are methyl, and the X group is oxygen.

In a fourth embodiment of this invention, a method for forming a chiral auxiliary is provided. First of all, an initiator is provided with the following structure:

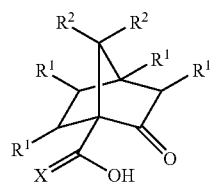

wherein $R^1$ and $R^2$ groups are independently hydrogen or $C_1$ to $C_{10}$ alkyl, X group is oxygen, two hydrogen atoms, or sulfur. More preferred are those moieties where the $R^1$ groups are hydrogen, the $R^2$ groups are methyl, and the X group is oxygen. Next, a hydrazine derivative $H_2NNHY$ is provided, wherein Y group is a functional group with stereo effect, as described in the first embodiment. Then, a dehydration reaction is performed of the hydrazine derivative $H_2NNHY$ with the initiator to produce an imine with the following structure,

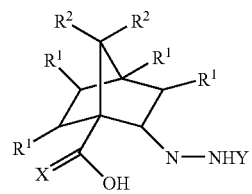

When the initiator is used in an amount of 1 equivalent, the hydrazine derivative $H_2NNHY$ is used in an amount more than 1 equivalent, and a preferred amount of $H_2NNHY$ is 1.2 equivalents. On the other hand, the dehydration reaction is performed in dichloromethane ($CH_2Cl_2$), and the operation temperature of the dehydration reaction ranges from 25° C. to 30° C.

In this embodiment, after the dehydration reaction, a cyclization reaction of the imine is performed to produce an amide with the following structure,

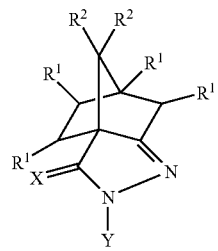

The cyclization reaction is a one-pot reaction. In a better case of this embodiment, the cyclization reaction further comprises an acylhalogenation step and a dehalogenation step, wherein the acylhalogenation step is performed to react $SOZ_2$, wherein Z is F, Cl, Br or I, with the imine to produce a mediate with the following structure:

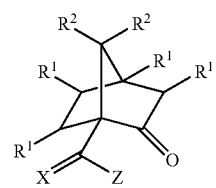

When the imine is used in an amount of 1 equivalent, the $SOZ_2$ is used in an amount more than 2 equivalents, and a preferred amount of $SOZ_2$ is 2.4 equivalents. Moreover, in this better case, the cyclization reaction is performed in ethyl acetate (EA), and the operation temperature of the cyclization reaction ranges from 50° C. to 80° C.

In this embodiment, after the cyclization reaction, a reduction reaction is performed of the amide with a reducing agent to produce a first chiral auxiliary with the following structure,

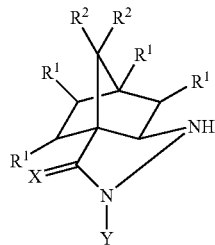
(I)

Next, an elimination reaction is performed of the first chiral auxiliary with a Lewis base without hydroxyl group to produce a second chiral auxiliary with the following structure.

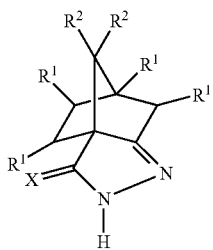
(II)

In a better case of this embodiment, the Lewis base further comprises sodium cyanoborohydride ($NaCNBH_3$). When the amide is used in an amount of 1 equivalent, the reducing agent is used in an amount more than 15 equivalents, and a preferred amount of the reducing agent is 18 equivalents. Moreover, the reduction reaction is performed in acetic acid (AcOH), and the operation temperature of the reduction reaction ranges from 25° C. to 30° C.

EXAMPLE 2

As shown in scheme 2, (+)-ketopinic acid 1 (20.00 g, 109.76 mmole) was dissolved in 150 mL $CH_2Cl_2$. Next, p-toluenesulfonhydrazide ($H_2NNH$-Ts) (28.62 g, 153.66 mmole) was added, under a nitrogen atmosphere, and the temperature is kept on room temperature (from 25° C. to 30° C.). After stirring for approximately 1 hr, the resulting solution is clear. The reaction was then quenched via addition of water. The organic layers were extracted with $CH_2Cl_2$, dehydrated with anhydrous magnesium sulfate. After filtration and primary drying, products are washed by cyclohexane and $CH_2Cl_2$ for 2 or 3 times, and then vacuum dried to form white solid 2. Finally, white solid 2 was recrystallied to form a colorless and transparent solid (36.54 g, yield 95%).

Compound 2 (9.00 g, 25.70 mmole) was dissolved in 660 mL ethyl acetate (EA). Next, $SOCl_2$ (7.34 g, 61.69 mmole) was added, heated to 60° C. to 80° C., and reflux for 5 hrs. The reaction was then quenched via addition of water. The organic layers were extracted with EA, dehydrated with anhydrous magnesium sulfate. After filtration and vacuum drying, products are purified by column chromatography with eluant (hexane:ethyl acetate=3:1) to form compound 3 (6.66 g, yield 78%). Finally, compound 3 was recrystallied to form a colorless and transparent solid.

Compound 3 (4.00 g, 12.04 mmole) was dissolved in 60 mL acetic acid (AcOH). Next, $NaCNBH_3$ powders (13.62 g, 216.79 mmole) were added for several batches. In the first batch, part of $NaCNBH_3$ powders was added, under a nitrogen atmosphere, and the temperature is kept on room temperature (from 25° C. to 30° C.), then followed by TLC. After all of the $NaCNBH_3$ powders were added, The reaction was then quenched via addition of water. The organic layers were extracted with $CH_2Cl_2$, dehydrated with anhydrous magnesium sulfate. After filtration and vacuum drying, products are purified by column chromatography with eluant (hexane:ethyl acetate=2:1) to form compound 4 (3.86 g, yield 96%). Finally, compound 4 was recrystallied to form a colorless and transparent solid.

Compound 4 (2.00 g, 5.99 mmole) was dissolved in 30 mL $CH_2Cl_2$. Next, triethylamine ($Et_3N$) (1.21 g, 11.97 mmole) was added, under a nitrogen atmosphere, and the temperature is kept on room temperature. After stirring for approximately 12 hrs, the reaction was quenched via addition of water. The organic layers were extracted with $CH_2Cl_2$, dehydrated with anhydrous magnesium sulfate. After filtration and vacuum drying, compound 5 is obtained. Finally, compound 5 was recrystallied to obtain a colorless and transparent solid (1.01 g, yield 95%).

$^1$H NMR:

$^1$H NMR ($CDCl_3$, 200 MHz) δ 8.56 (bs, 1H), 2.62 (ddd, J=17.6, 4.0, 2.6 Hz, 1H), 2.36-2.05 (m, 4H), 1.73 (td, J=9.9, 3.7 Hz, 1H), 1.5 (td, J=8.4, 2.9 Hz, 1H), 1.22 (s, 3H), 0.97 (s, 3H)

$^{13}$C NMR:

$^{13}$C NMR ($CDCl_3$, 200 MHz) δ 176.7, 175.5, 62.5, 49.7, 49.4, 32.0, 26.9, 25.3, 19.0, 18.5

X-ray Crystallographic Analysis:

Crystal data for Compound 5. $H_2O$ at −73° C. : $C_{10}H_{16}N_2O_2$, M 196.25, Orthorhombic, $P2_12_12_1$, a=6.7310 (2) Å, b=11.5370(4) Å, c=13.3580(6) Å, V=1037.32(7) Å$^3$, Z=4, $D_x$=1.257 Mg/m$^3$, μ=0.088 mm$^{-1}$, 1788 reflections, 128 parameters, R=0.0564, $R_w$=0.1314 for all data.

SCHEME 2

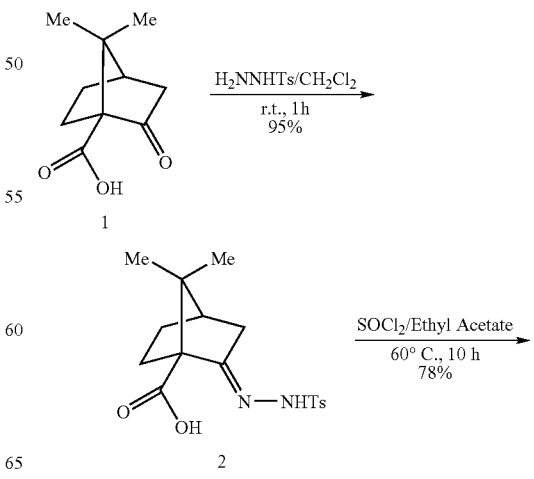

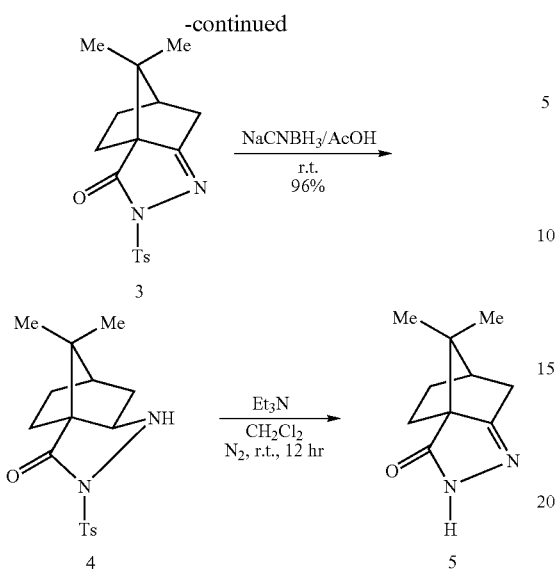

As described above, a main object of the present invention is to employ an initiator which is commercially available, and by reacting a hydrazine derivative with the initiator to introduce a functional group with stereo effect into the wanted compound. Then, a cyclization reaction (amidation) is performed to fabricate the chiral auxiliary. The fabrication method disclosed in this invention did have the advantages of simple procedure, good selectivity, and high yield. Therefore, this present invention does have the economic advantages for industrial applications.

Accordingly, the present invention discloses two kinds of camphor-derived chiral auxiliaries with general formula (I) and (II),

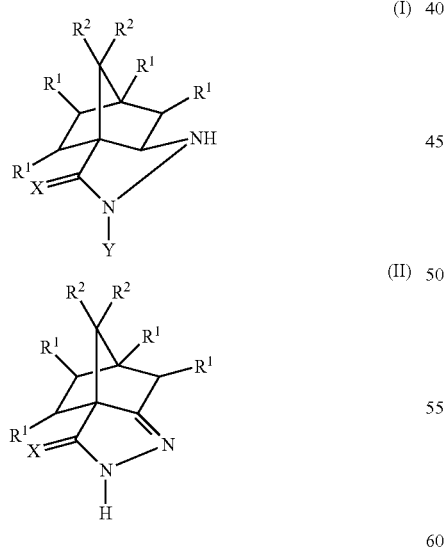

wherein $R^1$ and $R^2$ groups are independently hydrogen or $C_1$ to $C_{10}$ alkyl, X group is oxygen, two hydrogen atoms, or sulfur, and Y group is a functional group with stereo effect.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A compound of the formula:

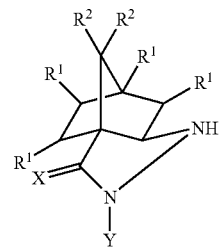

wherein $R^1$ and $R^2$ groups are independently hydrogen or $C_1$ to $C_{10}$ alkyl, X group is oxygen, two hydrogen atoms, or sulfur, and Y group has the following structure:

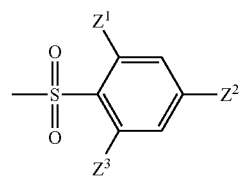

wherein $Z^1$, $Z^2$ and $Z^3$ are independently selected from the group consisting of: H, $CH_3$, $CH(CH_3)_2$, I, Br, Cl, nitrile group, $NO_2$, phenyl group and allyl group.

2. The compound according to claim 1, wherein said Y group is p-tolunesulfonyl with a structure as the following.

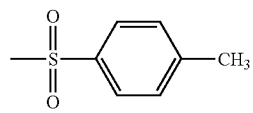

3. A method for forming a chiral auxiliary, comprising:
providing an initiator with a general formula as following:

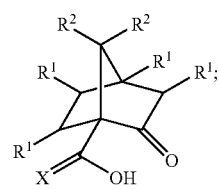

wherein $R^1$ and $R^2$ groups are independently hydrogen or $C_1$ to $C_{10}$ alkyl, X group is oxygen, two hydrogen atoms, or sulfur;

providing a hydrazine derivative $H_2NNHY$, wherein Y group has the following structure:

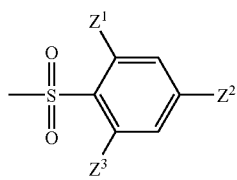

wherein $Z^1$, $Z^2$ and $Z^3$ are independently selected from the group consisting of: H, $CH_3$, $CH(CH_3)_2$, I, Br, Cl, nitrile group, $NO_2$, phenyl group and allyl group;

performing a dehydration reaction of said hydrazine derivative $H_2NNHY$ with said initiator to produce an imine with the following structure,

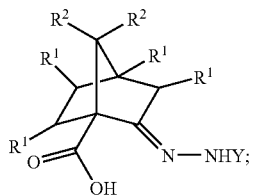

performing a cyclization reaction of said imine to produce a amide with the following structure,

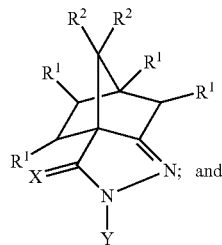

performing a reduction reaction of said amide with a reducing agent to produce said chiral auxiliary with a structure as the following,

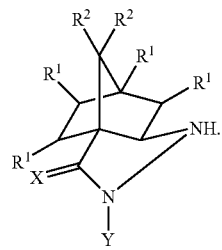

4. The method according to claim 3, wherein said Y group is p-tolunesulfonyl with a structure as the following,

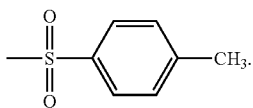

5. The method according to claim 3, wherein said dehydration reaction is performed in dichloromethane ($CH_2Cl_2$).

6. The method according to claim 3, wherein said cyclization reaction further comprises an acylhalogenation step and a dehalogenation step.

7. The method according to claim 3, wherein said cyclization reaction is a one-pot reaction.

8. The method according to claim 6, wherein said acylhalogenation step is performed to react said imine with $SOZ_2$, wherein Z is F, Cl, Br or I, so as to produce an intermediate with a structure as the following,

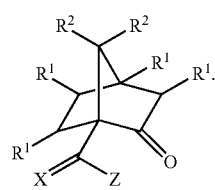

9. The method according to claim 3, wherein said cyclization reaction is performed in ethyl acetate (EA).

10. The method according to claim 3, wherein said reducing agent further comprises sodium cyanoborohydride ($NaCNBH_3$).

11. The method according to claim 3, wherein said reduction reaction is performed in acetic acid (AcOH).

12. A method for forming a chiral auxiliary, comprising:
providing p-toluenesulfonhydrazide ($H_2NNH$-Ts) and (+)-ketopinic acid with the following structure:

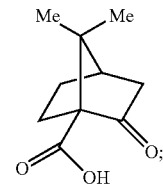

in dichloromethane ($CH_2Cl_2$), performing a dehydration reaction of p-toluenesulfonhydrazide ($H_2NNH$-Ts) with (+)-ketopinic acid to produce an imine with the following structure,

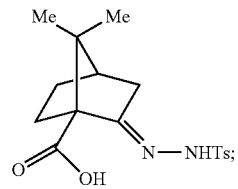

in ethyl acetate (EA), performing a cyclization reaction of said imine to produce an amide with the following structure,

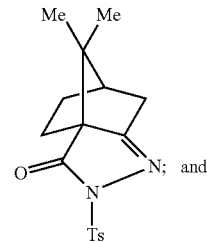

in acetic acid (AcOH), performing a reduction reaction of said amide with a reducing agent to produce said chiral auxiliary with the following structure,

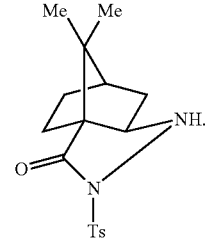

13. The method according to claim 12, when the (+)-ketopinic acid is used in an amount of 1 equivalent, the $H_2NNH$-Ts is used in an amount of 1.2 equivalents.

14. The method according to claim 12, wherein said cyclization reaction is a one-pot reaction, and said cyclization reaction further comprises an acylhalogenation step and a dehalogenation step.

15. The method according to claim 14, wherein said acylhalogenation step is performed to react $SOCl_2$ with said imine to produce a mediate with the following structure:

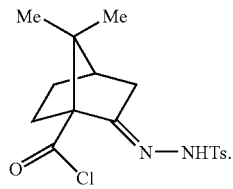

16. The method according to claim 15, wherein when said imine is used in an amount of 1 equivalent, the $SOCl_2$ is used in an amount of 2.4 equivalents.

17. The method according to claim 12, wherein said reducing agent further comprises sodium cyanoborohydride ($NaCNBH_3$).

18. The method according to claim 17, wherein when said amide is used in an amount of 1 equivalent, the $NaCNBH_3$ is used in an amount of 15 equivalents.

19. A chiral auxiliary with the following structure,

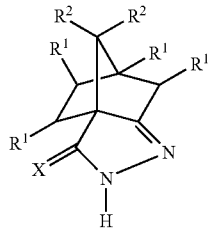

wherein $R^1$ and $R^2$ groups are independently hydrogen or $C_1$ to $C_{10}$ alkyl, and X group is oxygen, two hydrogen atoms, or sulfur.

20. A method for forming a chiral auxiliary, comprising:

providing an initiator with a general formula as following:

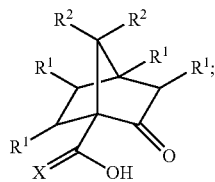

wherein $R^1$ and $R^2$ groups are independently hydrogen or $C_1$ to $C_{10}$ alkyl, X group is oxygen, two hydrogen atoms, or sulfur;

providing a hydrazine derivative $H_2NNHY$, wherein Y group has the following structure:

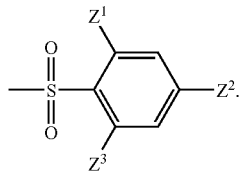

Wherein $Z^1$, $Z^2$ and $Z^3$ are independently selected from the group consisting of: H, $CH_3$, $CH(CH_3)_2$, I, Br, Cl, nitrile group, OR, NR, $NO_2$, phenyl group, allyl group, wherein R is alkyl group;

performing a dehydration reaction of said hydrazine derivative $H_2NNHY$ with said initiator to produce an imine with the following structure,

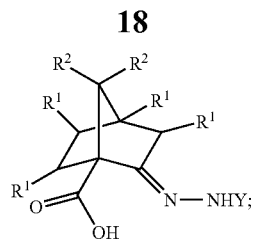

performing a cyclization reaction of said imine to produce a amide with the following structure,

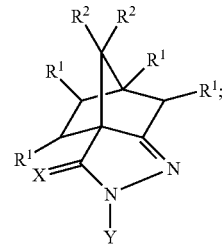

performing a reduction reaction of said amide with a reducing agent to produce a first chiral auxiliary with the following structure,

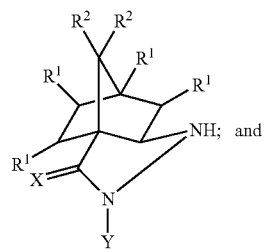

performing an elimination reaction of said first chiral auxiliary with a Lewis base without hydroxyl group to produce a second chiral auxiliary with the following structure,

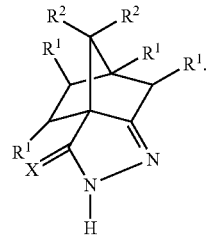

21. The method according to claim 20, wherein said Lewis base further comprises triethylamine ($Et_3N$).

22. A method for forming a chiral auxiliary, comprising:

providing p-toluenesulfonhydrazide ($H_2NNH$-Ts) and (+)-ketopinic acid with the following structure:

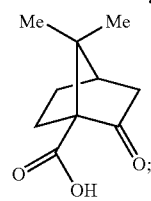

In dichloromethane ($CH_2Cl_2$), performing a dehydration reaction of p-toluenesulfonhydrazide ($H_2NNH$-Ts) with (+)-ketopinic acid to produce an imine with the following structure, In ethyl acetate (EA), performing a cyclization reaction of said imine to produce a amide with the following structure,

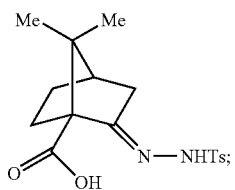

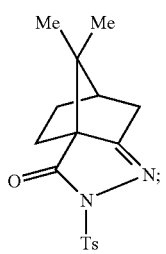

In acetic acid (AcOH), performing a reduction reaction of said amide with a reducing agent to produce a first chiral auxiliary with the following structure,

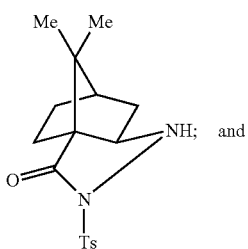

In dichloromethane ($CH_2Cl_2$), performing an elimination reaction of said first chiral auxiliary with triethylamine ($Et_3N$) to produce a second chiral auxiliary with the following structure,

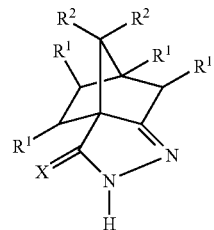

* * * * *